US009733136B2

(12) United States Patent
Seitz

(10) Patent No.: US 9,733,136 B2
(45) Date of Patent: Aug. 15, 2017

(54) TEXTILE PRESSURE SENSOR

(71) Applicant: Peter Seitz, Munich (DE)

(72) Inventor: Peter Seitz, Munich (DE)

( * ) Notice: Subject to any disclaimer, the term of this patent is extended or adjusted under 35 U.S.C. 154(b) by 160 days.

(21) Appl. No.: 14/378,867

(22) PCT Filed: Feb. 15, 2013

(86) PCT No.: PCT/EP2013/000455
§ 371 (c)(1),
(2) Date: Aug. 14, 2014

(87) PCT Pub. No.: WO2013/120624
PCT Pub. Date: Aug. 22, 2013

(65) Prior Publication Data
US 2016/0018274 A1    Jan. 21, 2016

(30) Foreign Application Priority Data

Feb. 16, 2012  (DE) .................. 10 2012 101 250
May 3, 2012   (DE) .................. 10 2012 103 856

(51) Int. Cl.
*G01L 1/14* (2006.01)
*G01D 5/241* (2006.01)
(Continued)

(52) U.S. Cl.
CPC .............. *G01L 1/14* (2013.01); *A61B 5/00* (2013.01); *A61B 5/6801* (2013.01);
(Continued)

(58) Field of Classification Search
None
See application file for complete search history.

(56) References Cited

U.S. PATENT DOCUMENTS 4,794,365 A * 12/1988 Dunbar ................ G01G 3/14
                                                   338/114
7,208,960 B1 * 4/2007 Deangelis ............ G01D 5/2405
                                                   324/661
(Continued)

FOREIGN PATENT DOCUMENTS

DE    3704870    4/1988
EP    0172784    2/1986
(Continued)

OTHER PUBLICATIONS

International Search Report for International Application No. PCT/EP2013/000455, mailed Jun. 18, 2013, 2 pgs.

*Primary Examiner* — Andre Allen
(74) *Attorney, Agent, or Firm* — Hamre, Schumann, Mueller & Larson, P.C.

(57) ABSTRACT

A textile pressure sensor for the capacitive measuring of a pressure distribution of objects of any shape, in particular body parts, on a surface is proposed, having a first structure (30*a*) which is conductive at least in regions and a second structure (30*b*) which is conductive at least in regions, wherein the first and the second structure which are conductive at least in regions are separated from each other by a dielectric intermediate element (48), and wherein conductive regions of the first structure (30*a*) form capacitors with opposite conductive regions of the second structure (30*b*). The textile pressure sensor is distinguished in that the first and/or the second structure (30*a*, 30*b*) which is conductive at least in regions is designed as a knitted fabric.

14 Claims, 4 Drawing Sheets

(51) Int. Cl.
   *A61B 5/00*      (2006.01)
   *H01G 13/00*    (2013.01)
(52) U.S. Cl.
   CPC ......... *A61B 5/6843* (2013.01); *G01D 5/2417*
          (2013.01); *G01L 1/146* (2013.01); *H01G*
                                 *13/006* (2013.01)

(56)             References Cited

U.S. PATENT DOCUMENTS

| | | |
|---|---|---|
| 2002/0121146 A1 | 9/2002 | Manaresi et al. |
| 2007/0186667 A1* | 8/2007 | Deangelis ............ G01D 5/2405 73/780 |
| 2007/0248799 A1* | 10/2007 | DeAngelis .............. G01L 1/146 428/209 |
| 2012/0323501 A1* | 12/2012 | Sarrafzadeh .......... A61B 5/1116 702/41 |
| 2014/0238151 A1* | 8/2014 | Dunne .................... D05B 97/12 73/862.474 |
| 2016/0186366 A1* | 6/2016 | McMaster ................ D04B 1/14 66/202 |

FOREIGN PATENT DOCUMENTS

| | | | | |
|---|---|---|---|---|
| EP | 1927825 | | 6/2008 | |
| ES | 2682724 A1 | * | 1/2014 | ........... G01L 9/0052 |
| GB | WO 2005073685 A1 | * | 8/2005 | ............. D02G 3/441 |
| GB | 2443208 A | * | 4/2008 | ............. D03D 1/0088 |
| IT | WO 2015014950 A1 | * | 2/2015 | ............. G01L 1/205 |
| WO | 2005/121729 | | 12/2005 | |

\* cited by examiner

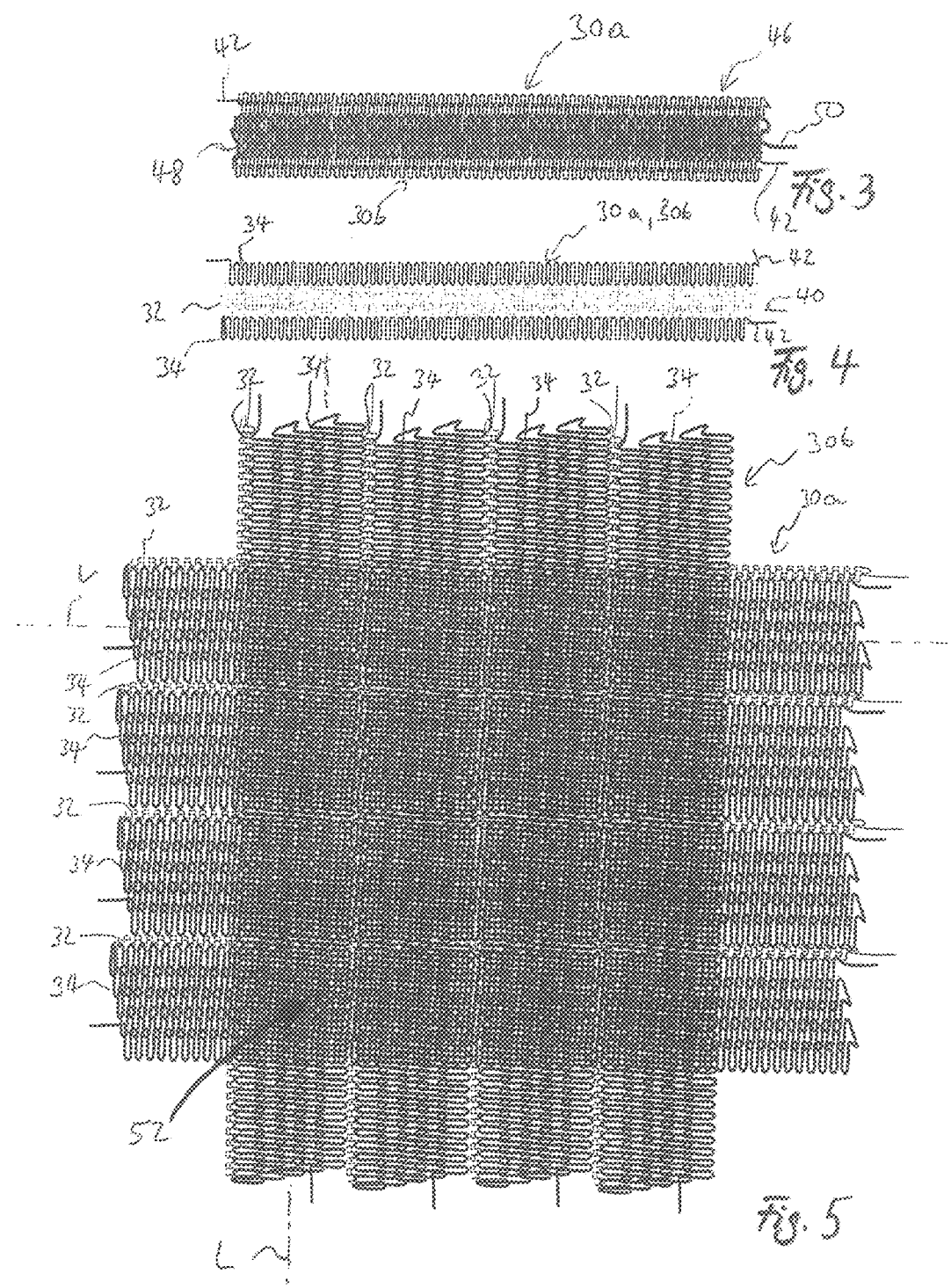

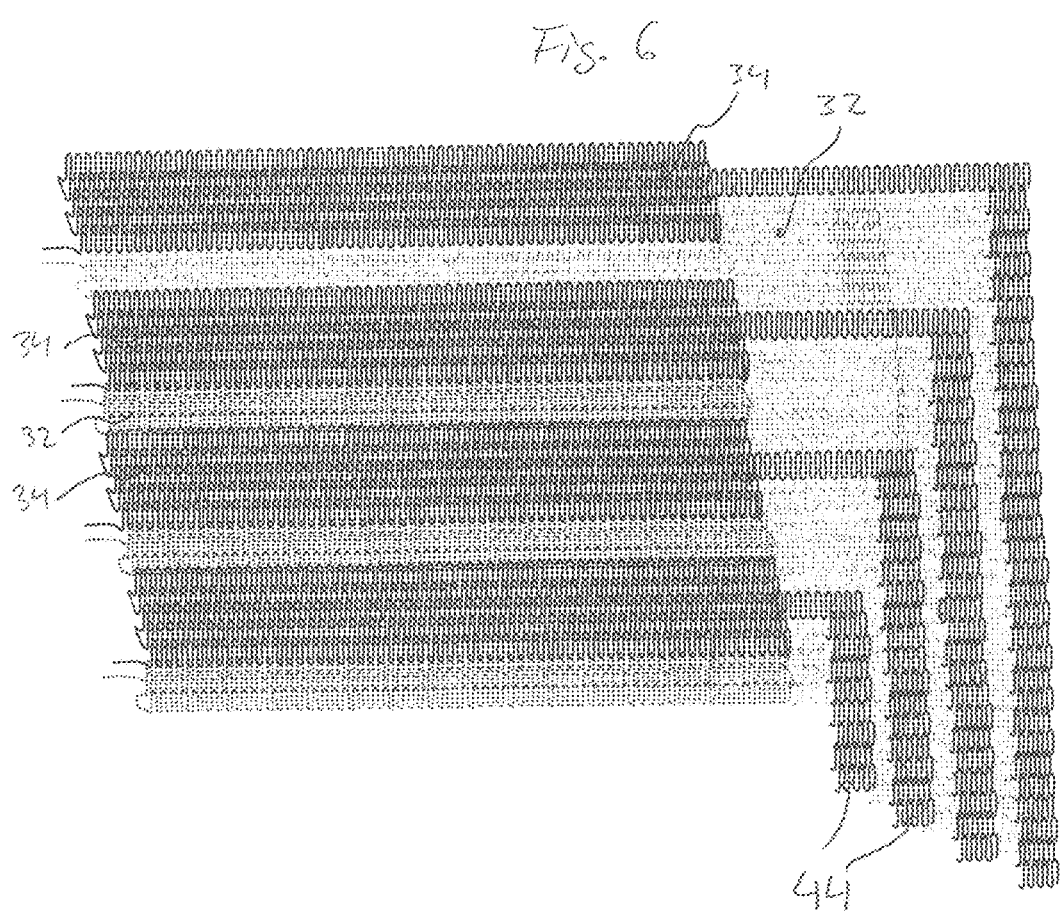

TEXTILE PRESSURE SENSOR

FIELD OF THE INVENTION

The invention relates to a textile pressure sensor for the capacitive measuring of a pressure distribution on a surface in accordance with the preamble of Claim 1, and to a production method in accordance with the preamble of Claim 10.

BACKGROUND

A textile pressure sensor for the capacitive measuring of the pressure distribution on a surface is known for example from DE 37 04 870, and exhibits a matrix arrangement of strips of conductive foil which are isolated from each other. The arrangement is flexible but not extensible.

A generic pressure sensor 1 for the capacitive measuring of a pressure distribution on a surface which is known from WO 2005/121729 is shown in the appended FIG. 7. The pressure sensor 1 is mat-shaped, i.e. formed substantially flat, and comprises a first conductive structure 3 and a second conductive structure 5. Between the first and the second conductive structure, which comprise a woven fabric, there is arranged a dielectric intermediate element 7 which is designed to be reversibly compressible, for example made of felt or foam. The first and the second structure are therefore arranged lying opposite one another. The first structure 3, which in FIG. 7 forms the upper side of the textile pressure sensor 1, comprises a plurality of conductive regions 9, i.e. electrodes which are electrically isolated from each other. Each conductive region 9 is connected in each case via a connecting lead, not shown in FIG. 7, to an electric circuit for the purpose of supplying energy and for evaluation. That surface or side which comes into contact with an object, the pressure distribution of which is to be measured on the textile pressure sensor 1, in this case is designated the upper side of the textile pressure sensor 1. In the embodiment shown, the second structure 5 has a continuously conductive surface, but it is likewise conceivable to provide several conductive regions which are isolated from each other, corresponding to the first structure 3. The second structure 5 forms the underside of the textile pressure sensor 1, which is arranged substantially parallel to the upper side of the pressure sensor. Owing to the opposite arrangement of conductive regions, capacitors C are formed between the first structure 3 and the second structure 5 in regions of overlap 11.

A capacitive sensor which is constructed as an individual sensor is known from EP 1 927 825 A1. In this case, fabrics to which foils are applied as capacitor plates are used. The fabrics may also be in the form of knitted fabrics.

A similar construction in which conductive or non-conductive fabrics are used is known from US 2007/0248799 A1. Here too, the term "fabric" is also to be understood to mean knitted goods, i.e. knitted fabrics or warp-knitted fabrics. Here too, the known construction is very labor-intensive.

The method of operation of capacitive sensors is sufficiently known. They operate on the basis of the change in the capacitance of an individual capacitor or of a whole capacitor system. Virtually all capacitive sensors are based on the principle that two plates form an electrical capacitor, one plate of which is displaced or deformed by the effect which is to be measured. As a result, the plate spacing, and hence the electrically measurable capacitance, changes. In order also to be able to detect small changes better, the actual measuring electrode is frequently surrounded by a shielding electrode which shields the non-homogeneous edge region of the electric field from the measuring electrode. This yields an approximately parallel electric field with the known characteristic of an ideal plate-type capacitor between the measuring electrode and the usually earthed counter-electrode. In the case of a capacitive pressure sensor, the change in capacitance as a result of the deflection of a membrane and of the resulting change in the plate spacing is evaluated as a sensor effect. The membrane in this case is formed as a capacitor plate. The changes in capacitance are fairly small, so suitable processing electronics of high sensitivity must be integrated into it.

In relation to the textile pressure sensor 1, this means that for measuring a pressure distribution an object comes into contact with the upper side of the textile pressure sensor 1. The object in so doing exerts a compressive force on the textile pressure sensor 1 in the direction of the arrow 13, which brings about compression of the dielectric intermediate layer 7. In other words, the distance between the conductive regions 9 of the structures 3 and 5 is reduced where the force is exerted on the upper side of the textile pressure sensor 1 by the object.

The compression of the intermediate layer 7 and hence a reduction in the distance between the structures 3 and 5 is greatest where the greatest compressive force is exerted on the upper side of the textile pressure sensor 1. Correspondingly, the change in capacitance, which is detected by connected evaluation electronics, will be greatest in the regions of the greatest application of force or of the greatest pressure. The conductive regions 9 are preferably arranged in a matrix, and thus produce a matrix-shaped arrangement of capacitors C which preferably span the entire surface of the textile pressure sensor 1. Due to the detection of the capacitance and in particular of the change in capacitance of each capacitor C, a pressure-distribution pattern can thus be generated by the textile pressure sensor 1.

The use of textile pressure sensors of the type mentioned here is not restricted to a specific field. Rather, they can be used in many different ways, for example in the field of medical engineering, orthopaedics or sport. For example, textile pressure sensors can be used in medical engineering in order to avoid decubitus ulcers, i.e. local damage to the skin and the underlying tissue due to pressure being exerted on a patient's body parts. Such decubitus ulcers may for example occur in patients who are confined to bed or to a wheelchair. Textile pressure sensors can be used to measure the two-dimensional pressure distribution of a body part on an undersurface, for example on a mattress or the like, and to identify pressure points. In the field of medical engineering, furthermore the pressure distribution when a candidate is walking may for example provide information about orthopaedic damage or alternatively sensory damage (e.g. in diabetics).

In orthopaedics, textile pressure sensors of the type mentioned here may serve to detect the pressure distribution of a foot on the sole of a shoe. On the basis of the detected pressure distribution, the sole of the shoe can then be adapted, in particular by producing an individual insole, such that pressure peaks between the foot and the shoe material are avoided. In particular in the case of sports shoes or ski boots, such individual adaptation of shoes and boots is of particular interest. For example, it is of interest to the producer of sports shoes how the active forces are distributed across the foot surface of the wearer of the shoe during walking or running movements. Correspondingly, the shoes can be optimised according to the field of application.

Resilient or supportive elements can accordingly be arranged in the shoe. This results in optimal adaptation of the shoe to the wearer, with the individual force distribution which occurs dependent on the anatomy of the wearer of the shoe and the sequences of movement thereof being taken into consideration. In the field of sport, a textile pressure sensor may furthermore serve to detect the pressure distribution in the production of skis, in order to be able to adapt a core structure accordingly. It is also conceivable in principle to use a textile pressure sensor for optimising bicycle saddles or equestrian saddles.

Further fields of application are pressure-sensitive floor coverings, in order to be able to detect a movement of an object or a load or a change in loading of a floor in a building in differentiated manner. Textile pressure sensors are further used in the field of synthetic skins for robots in order to reproduce tactile senses. Textile pressure sensors are also used for seating of any kind, in particular adaptive seats for aircraft, motor vehicles, drivers' cabs or in the private sphere, such as for example for office chairs. Textile pressure sensors are also used in the field of medical diagnostics for measuring the two-dimensional distribution of compressive forces. A further field of application is the measuring of muscle strength, in particular of sphincters at or in body orifices. Furthermore, it is conceivable to use textile pressure sensors in the field of video-game consoles, in particular for detecting a position and movements of a person and converting them into corresponding movements of gaming characters or gaming elements on a screen. Textile pressure sensors can also be used for identifying people, with the individual pressure-distribution patterns for example of a hand or a foot being used for unambiguous identification.

In summary, textile pressure sensors of the type mentioned here can be used everywhere where objects in general, and in particular body parts of a person, lie on a substantially solid substrate. Many objects and in particular body parts, the pressure distribution on a substrate of which is to be measured, are however not flat, but formed irregularly with elevations and depressions. Good adaptability to uneven objects and considerable robustness in the event of loading by such objects are thus a crucial quality criterion for textile pressure sensors. It has however been shown that the known textile pressure sensors for the capacitive measuring of a pressure distribution meet this quality criterion only to a limited extent.

SUMMARY OF INVENTION

It is therefore an object of the present invention to provide a textile pressure sensor which has good adaptability to uneven surfaces and objects, and also considerable robustness in the event of loading by objects.

In order to achieve the above object, a textile pressure sensor having the features of Claim 1 is proposed. The textile pressure sensor serves for the capacitive measuring of a pressure distribution of an object of any shape, in particular a body part, on a surface, and has a first structure which is conductive at least in regions and a second structure which is conductive at least in regions, wherein the first and the second structure which are conductive at least in regions are separated from each other by a dielectric intermediate element, and wherein conductive regions of the first structure form capacitors with opposite conductive regions of the second structure. The textile pressure sensor is distinguished in that the first and/or the second structure which is conductive at least in regions is designed as a knitted fabric.

At this point, it should be mentioned that "knitted fabric" is also to be understood below to mean "warp-knitted fabric", embroidered or crocheted goods, i.e. (knitted) goods in which one or more threads are interlaced in and with each other. A loose non-woven fabric will therefore also come under this heading. Furthermore, it should be mentioned that "thread" is to be understood to mean not only formations of joined/twisted fibres but also monofilaments. It should likewise be mentioned that "threads", when they are supposed to be conductive, may be constructed from conductive and non-conductive fibres.

An essential point of the invention is thus that the textile pressure sensor according to the invention can also optimally measure the pressure distribution of unevenly shaped objects without there being any risk of tearing or similar damage in a direction of pull of the textile pressure sensor. The pressure sensor is designed to be particularly robust by the use of a knitted fabric, since the knitted fabric, in contrast to a woven fabric, is extensible in all directions. A knitted fabric is as a rule distinguished in that it is produced in regions from a single thread or yarn, the thread or the yarn being interlaced in knit-stitch-like loops (stitches). A knitted fabric therefore, in contrast to a woven fabric, which has warp and weft threads, has rows of stitches (and columns of stitches) which yield a coherent knitted fabric (or warp-knitted fabric). The knitted fabric as a result can adapt particularly well to a body or to the shape thereof. A further advantage of the pressure sensor according to the invention is the many forms which the sensor can assume due to the use of a knitted fabric. In particular, the textile pressure sensor can also be knitted in a three-dimensional shape (e.g. as a stocking or glove), which again is not readily possible with other materials, even if they have great extensibility in all directions. This advantage is obtained by designing the first and/or the second structure which is conductive at least in regions as a knitted fabric. The knitted fabric is particularly advantageous because, in contrast to a woven fabric, it may also be formed of only a single thread or yarn, the thread or yarn possibly being very thin and having a high stitch density. Textile pressure sensors which according to the invention comprise a knitted fabric can thus be used for any imaginable individual use, in particular also for enveloping complicated three-dimensional shapes. For example, it is conceivable to knit a tubular or even spherical knitted fabric for a textile pressure sensor for the capacitive measuring of a pressure distribution. Due to the knitted fabric which comprises knit stitches, the textile pressure sensor is designed to be elastic both in the longitudinal direction and in the transverse direction solely because of the curved thread paths, and thus has considerably increased extensibility or flexibility compared with other materials, such as for example a woven fabric, the tear strength of the sensor according to the invention also being considerably increased. A knitted fabric is furthermore particularly soft and smooth, and can thus advantageously be used for articles of clothing such as socks, trousers or pullovers, or alternatively as a cover for a motor-vehicle seat. Furthermore, the knitted fabric does not tend to wrinkle, and is thus particularly well-suited for use in textile pressure sensors.

According to the invention, provision is made for the first and/or the second structure which is conductive at least in regions to be designed as a knitted fabric. For example, it is conceivable to produce only the upper side of the textile pressure sensor which faces the object to be measured, i.e. the first structure, from a knitted fabric, in order to increase the comfort of the textile pressure sensor in particular in the field of articles of clothing. Provision may however also be made for merely the underside of the textile pressure sensor which is remote from the object, i.e. the second structure, to be designed as a knitted fabric, for example in order to increase the ability of the sensor to adapt to a substrate. An embodiment in which both the first and the second structure are designed as a knitted fabric is particularly preferred. This achieves maximum flexibility of the sensor.

Furthermore, it is possible also to produce the conductive structures from non-conductive material by additive methods, i.e. applying conductive material (e.g. electroplating, printing, vapour-deposition). Conversely, non-conductive regions can be produced by subtractive methods, e.g. by etching or cutting.

In order to produce a conductive region or a plurality of conductive regions in the first and/or in the second structure, preferably conductive threads are incorporated, i.e. knitted, into the knitted fabric during the knitting operation. The conductive regions may in particular be designed in the form of paths which are separated off, i.e. isolated from each other, of a conductive thread or yarn. A plurality of conductive regions of the knitted fabric which are isolated from each other may in each case comprise a plurality of adjacent rows of stitches of a conductive thread, filament or yarn. Modern industrial knitting machines make it possible to produce virtually any patterns and combinations of patterns whatsoever which the knitted fabric may comprise, in particular in order to form conductive regions. Modern knitting machines furthermore make it possible to work electrically conductive threads or yarns for example made of carbon fibres, high-grade steel, gold, silver or brass, in particular in the form of what are called "technical knits". In this case, the threads or yarns may themselves be elastic, but do not have to be, since the stitches themselves form yielding structures.

The conductive paths of the first structure are arranged at an angle, for example of 90 degrees, relative to the conductive paths of the second structure. If the second structure which forms the underside is designed to be conductive throughout, the arrangement of the conductive regions of the first structure relative to the conductive region of the second structure does not matter. However, it is then necessary to provide an island-like or matrix-like arrangement of separated-off conductive regions of the first structure, in order to ensure that a sufficient number of capacitors is formed.

What is crucial is that the first and the second structure, and in particular the conductive regions thereof, are arranged opposite one another such that the conductive regions form overlapping surfaces to form capacitors. For this, provision may of course also be made for the conductive paths to be at a more acute angle than 90° to each other, provided that both the first and the second structure have conductive paths which are isolated from each other. The conductive regions have corresponding connections to the evaluation electronics, which may likewise be knitted into the first and/or the second structure.

The knitted fabric furthermore advantageously makes it possible to incorporate or knit into the first and second structure connectors which serve for joining conductive regions to a power-supply source and to corresponding evaluation electronics. The connectors may for example be in the form of knob-shaped or stud-shaped connection elements which project beyond the material edge of the textile pressure sensor, and which are preferably part of the knitted fabric.

Furthermore, leads/connectors can be produced by gluing, soldering, welding, clamping or alternatively sewing.

As stated, the first and the second structure which are conductive at least in regions are preferably arranged opposite one another. Furthermore, the dielectric intermediate element is formed from a reversibly compressible material, so that after compression of the textile pressure sensor in one region the textile pressure sensor in this region can return again to its initial state. The dielectric intermediate element may likewise be designed as a knitted fabric. A warp-knitting method on a double Raschel machine, the dielectric intermediate element being produced by correspondingly-formed pile threads, is particularly suitable here. In this case, the knitted fabric or warp-knitted fabric is preferably formed from a reversibly compressible material, i.e. knitted with a corresponding thread or yarn. Provision may also be made for the dielectric intermediate element alternatively or additionally to have integrated restoring elements in the region of the overlapping surfaces of the conductive regions. These integrated restoring elements may be incorporated or knitted into the knitted fabric. In this manner, the flexibility and elasticity of the textile pressure sensor which is based on the knitted fabric is not adversely affected by the isolating material. For example, it is conceivable to form the integrated restoring elements exclusively in a plurality of rows of stitches which consist of a reversibly compressible and isolating yarn or filament and are arranged in the region of the overlapping surfaces of the conductive regions. Furthermore, it is conceivable to provide restoring elements merely in the region of island-like shapings, comprising a plurality of stitches of the knitted fabric.

In one embodiment of the invention, provision may be made for merely one of the two structures which are conductive at least in regions to be formed from a knitted fabric. For example, it is conceivable to form one of the two structures from a material which is conductive throughout and only to form the further, opposite, structure from a knitted fabric with integrated, i.e. knitted-on, conductive regions. Furthermore, it is conceivable to apply, in particular to print on or glue on, the conductive regions in a first or the second structure directly to the dielectric intermediate element, while the other structure is designed as a knitted fabric with knitted conductive regions.

In a further embodiment, both the first and the second structure may consist of a knitted fabric which has incorporated conductive regions which form overlapping surfaces to form capacitors. The dielectric intermediate element can then be formed for example as a foam layer or the like reversibly compressible element.

In one further embodiment of the invention, provision may be made for both the first and the second structure with the conductive regions and the dielectric intermediate element to be designed as a knitted fabric. Whereas conductive regions are knitted into the knitted fabric of the first and second structure which are conductive at least in regions, such conductive regions are not provided in the dielectric intermediate layer.

The layers of the textile pressure sensor may for example be sewn together by an isolating thread. This also applies when one or more layers of the textile pressure sensor are not designed as a knitted fabric.

Moreover, an embodiment of the invention in which the pressure sensor is formed from a single coherent web-like knitted fabric is conceivable. For example, it is conceivable to fold the web-like knitted fabric in an S-shape or Z-shape and then to join it, in particular to sew it, such that a three-layered mat-shaped textile pressure sensor is produced. The web-like knitted fabric then comprises preferably conductive paths which are joined via an isolating thread, which are formed and arranged such that, after folding, regions of overlap are formed between the first and the second structure to form capacitors, whereas the dielectric intermediate layer does not have any conductive regions. Rather, restoring elements may be introduced into the intermediate layer, or the part of the coherent web-like knitted fabric forming the intermediate layer can be knitted from a reversibly compressible material.

Provision may also be made for merely the first and the second structure of the textile pressure sensor to be formed in one piece from a single coherent web-like knitted fabric with (knitted) conductive regions or paths and between these (knitted) isolating rows of stitches. Then a separate dielectric intermediate element can be inserted between the two knitted structures which lie opposite each other, which element is joined to the first and the second structure.

Overall, it is shown that the textile pressure sensor according to the invention consists at least partially of a knitted fabric, which has considerable advantages compared with sensors made of a different material, in particular from a woven fabric or a foil. In a knitted fabric or warp-knitted fabric, it is for example advantageously possible, without losing the elasticity of the textile pressure sensor, to separate off paths made from a conductive thread or yarn from the rest of the, non-conductive, knitted fabric. The knitted fabric then comprises virtually knitted electrodes. In the case of textile pressure sensors which have glued-on electrodes, considerable deterioration results in particular with regard to the elasticity of the sensor.

The knitted fabric in accordance with the present invention preferably comprises alternating groups of rows of stitches made from a conductive and a non-conductive thread or yarn. Due to this arrangement, conductive and non-conductive paths alternate, with one path in each case possibly comprising a plurality of rows of stitches and a plurality of columns of stitches.

The number of capacitors of the textile pressure sensor depends on how many regions of overlap of conductive regions or electrodes are provided. It goes without saying that the number of capacitors is greater, the greater the number of conductive regions and hence regions of overlap. The number and distribution of the capacitors and hence the accuracy of the pressure-distribution measurement consequently depends on the "knitting pattern" of the electrodes, i.e. of the conductive regions.

It follows from the above that the invention also relates to a method for the production of a textile pressure sensor. From the point of view of production, weft-knitting or warp-knitting is a particularly advantageous production method, because very complicated structures can be produced "automatedly" by knitting machines/warp-knitting machines. Namely conductive regions for the formation of capacitor electrodes and/or connection paths and/or isolating regions for isolated joining of the capacitor electrodes can be knitted together, without a particularly large number of difficult steps having to be carried out by hand. In particular when the isolating regions are knitted on to the conductive regions, optimum mechanical connections are produced without the necessity of having to carry out cutting or gluing work, as has been the case hitherto in the case of woven fabrics, and even more in the case of foil structures.

Furthermore, further isolating regions for the formation of compressible capacitor dielectrics can also be knitted-in at least between opposite conductive regions which form capacitors, which isolating regions join the conductive regions together and are knitted into them. Therefore knitting is carried out three-dimensionally, so to speak.

The use, which is claimed here as being essential to the invention, of knitted fabrics or warp-knitted fabrics also has the further advantage that merely due to the stitch structure of a knitted fabric or warp-knitted fabric relatively soft and above all also extensible formations can be produced without extensible yarns or threads having to be used for this. Therefore even (as indicated above) monofilaments of metal or of plastics material (for the conductive or the non-conductive regions, respectively) can be used if the type of knitting is selected such that the required elasticity of the entire knitted fabric is ensured.

As follows from the above, one advantage of a textile capacitive pressure sensor, in particular one made from knitted goods, lies in its extensibility. This means that the surface area of a capacitor element can increase by up to 100%. However, this also has adverse effects:

a) If the resulting force from the pressure of the elements according to the formula $F=a*p$ (a=surface area; p=pressure), the force F is incorrect, since p [can] be measured, but a is now no longer a constant.
b) Since an increase in the surface area brings about the capacitance of the measuring capacitor, the measured pressure is higher than what is actually applied.
c) Upon extension of the pressure-absorbing dielectric, dependent on the design of the dielectric, the thickness thereof may decrease, which as previously described increases the measured pressure value.

Effects b) and c) may partially compensate for a), i.e. improve the accuracy of the force measurement. The error of the pressure measurement cannot be compensated thus.

Now the effects of the extension can be overcome:

A: Separate measurement of the extension
　a. A second layer which is only responsive to extension is arranged over the pressure-sensitive, extension-sensitive layer. This is achieved by an incompressible, elastic dielectric.
　b. Furthermore, pressure-sensitive and exclusively extension-sensitive sensor elements can be arranged in a single sensor matrix in that the dielectric is formed to be alternately pressure-sensitive or exclusively extension-sensitive. In this case, the localised resolution of the matrix must be so high that the differences in pressure or extension between adjacent sensor elements do not exceed a certain amount.
　c. The true pressure can be determined by a calibration algorithm.
　d. The three-dimensional deformation of the sensor matrix can be calculated by means of the measurement of the extension, in particular if the extension in the x-direction and y-direction is determined separately.

B: Formation as linear capacitor electrodes
　a. The capacitor plates are not regarded as homogeneous surfaces, but as separately parallel-extending conductive threads which are isolated from each other and the spacing of which is great compared with the counter-electrodes, so that the electric fields of adjacent threads are superposed only slightly. If the spacing of the threads changes upon extension, the totals of the capacitances formed by the individual threads will change only slightly.
　b. Such an arrangement can be manufactured easily by textile techniques (fabrics).
　c. If the counter-electrode is formed two-dimensionally, the capacitance upon extension transversely to the thread direction remains constant and increases upon extension in the thread direction.
　d. If the counter-electrode is likewise constructed from isolated threads, there are two cases, the capacitors in each case being formed linearly.

e. The threads extend parallel to the first electrode.
1. The thread-shaped electrodes lie in such a manner that the threads are located exactly opposite each other. The spacing between the electrodes is minimal.
   Upon extension transversely to the thread: The capacitance is constant.
   Lengthwise to the thread: The capacitance rises (as c. above).
2. As under number 1, but the threads are offset such that a maximum spacing between the electrodes is produced.
   Extension transversely to the thread: The capacitance decreases.
   Extension lengthwise to the thread: The capacitance increases.
3. The electrodes are arranged turned relative to each other by 90 degrees. The capacitors are rather formed in a dot-shape.
   Upon extension in each direction, the capacitance remains constant.

BRIEF DESCRIPTION OF THE DRAWINGS

The invention will be explained in greater detail below with reference to the drawings. These show:

FIG. 3 a diagrammatic sectional representation of a textile pressure sensor according to the invention;

FIG. 4 a diagrammatic top view of alternating groups of rows of stitches made of conductive and non-conductive threads according to the invention;

FIG. 5 a diagrammatic top view of a textile pressure sensor according to the invention;

FIG. 6 a further embodiment in a representation according to FIG. 5, and FIG. 7 a textile pressure sensor known from the prior art.

DETAILED DESCRIPTION OF THE DRAWINGS

Figure 1:
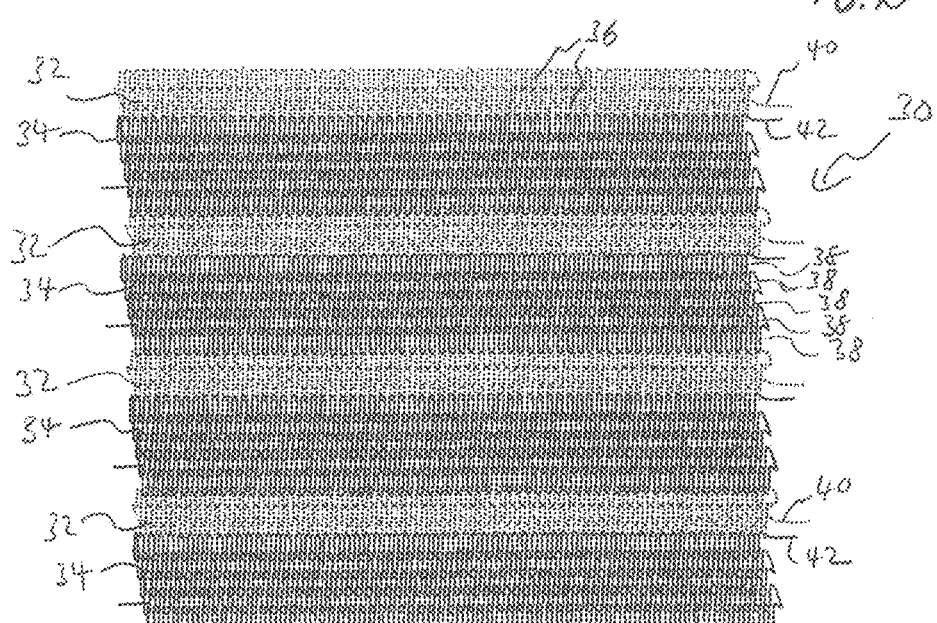
FIG. 1 a diagrammatic top view of a structure according to the invention which is conductive at least in regions and which is designed as a knitted fabric.
Figure 7:
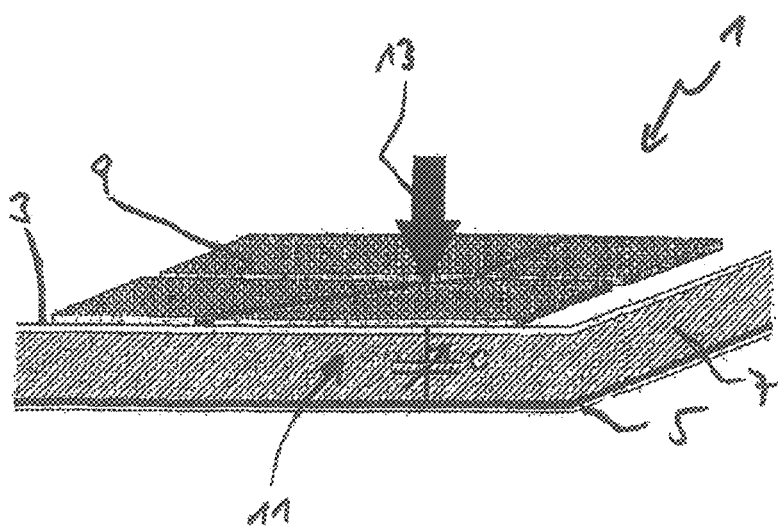

FIG. 1 shows a diagrammatic top view of a structure 30 which is electrically conductive at least in regions and which is designed as a knitted fabric. The structure 30 shown in FIG. 1 which is conductive at least in regions may form both the first and the second structure 3 or 5 which is conductive at least in regions shown in FIG. 7. The structure 30 which is conductive at least in regions in FIG. 1 comprises electrically non-conductive regions 32 illustrated by dotted lines, and electrically conductive regions 34 illustrated in dark ink. In the embodiment according to FIG. 1, each non-conductive region 32 comprises two rows of stitches 36 of a non-conductive filament or thread. The conductive regions 34 on the other hand comprise five rows of stitches 38 in each case. It goes without saying that the number of rows of stitches 36, 38 of the non-conductive or conductive regions 32, 34 respectively can be different. Preferably the non-conductive paths are made particularly narrow, and may therefore have merely a single row of stitches 36.

FIG. 1 makes it clear that each region 32 and 34 is knitted with a single thread 40 or 42 respectively. In this case, a conductive region 34 is knitted directly onto a non-conductive region 32. Correspondingly, also a non-conductive region 32 is knitted onto a thread 42 of a conductive region 34 with a thread 40. The thread 40 in this case is a thread made of an electrically non-conductive material, whereas the thread 42 is a thread made of an electrically conductive material. Correspondingly, the electrically conductive regions 34 form the electrodes of the structure 30. The thread 42 may also comprise both electrically conductive and non-conductive fibres.

Figure 2:
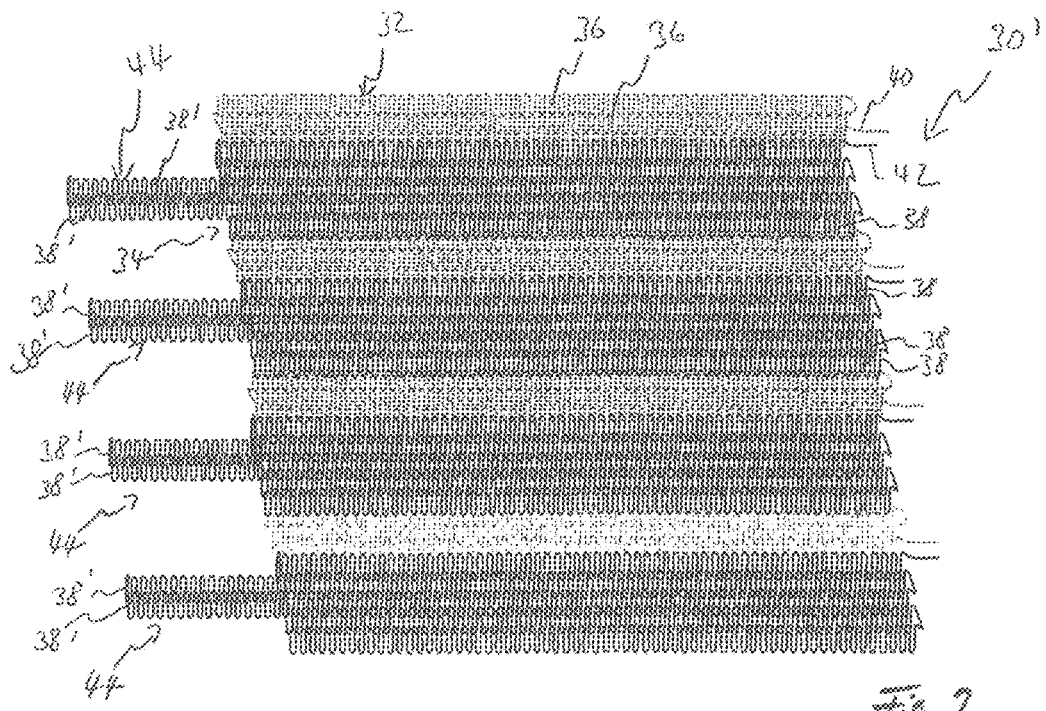
FIG. 2 a diagrammatic top view of a structure which is conductive at least in regions and which is designed as a knitted fabric, with connectors.

FIG. 2 shows a diagrammatic top view of a structure 30' which is conductive at least in regions, which is additionally provided with connectors 44. The connectors 44 serve to connect the conductive regions 34 to a power supply and/or to evaluation electronics. The connectors 44 in this case are knitted by means of the thread 42 which forms the conductive regions 34. In FIG. 2, the connectors 44 are formed by two rows of stitches 38' which are longer than the other rows of stitches 38 of the conductive regions 34, and which are also longer than the rows of stitches 36 of the non-conductive regions 32. The rows of stitches 36 of the non-conductive regions 32 and the rows of stitches 38 of the conductive regions 34 are moreover formed of equal length. The connectors 44 thus project beyond the edge of the knitted structure 30'. Alternatively, provision may be made for the connectors 44 to be formed separately, in particular to be knitted and then to be joined, for example stitched or alternatively knitted on, to the conductive regions 34, in particular in an edge region.

Overall, it is shown that alternating conductive and non-conductive paths are formed due to the alternating running-together in groups of rows of stitches made of an electrically conductive and a non-conductive thread or yarn. The conductive paths 34 are consequently electrically isolated from each other by the non-conductive paths.

FIG. 3 shows a diagrammatic sectional view of a textile pressure sensor 46 according to the invention. In the embodiment according to FIG. 3, both the first, upper, structure 30a which is conductive at least in regions and the second, lower, structure 30b which is conductive at least in regions are designed as knitted fabrics. The knitted fabric in such case may be formed as shown in FIGS. 1 and 2. Between the first and the second structure 30a and 30b which are conductive at least in regions, there is arranged an intermediate element 48 which is likewise designed as a knitted fabric and is elastically compressible. The intermediate element 48 is also formed from a single thread 50. The thread 50 is knitted to form a three-dimensional knitted fabric, which therefore has not only rows of stitches in a single plane, but which rather has rows of stitches in several planes which are knitted together. In this manner, a knitted dielectric intermediate element 48 having a plurality of stitch planes which is formed to be reversibly compressible can be provided. For this, the thread 50 does not even have to be extensible, but only flexible, since the stitch structure ensures the extensibility and compressibility of the arrangement. This moreover also applies to the threads 40 and 42 of the conductive or isolating regions respectively. Warp-knitting machines (double Raschel machines), on which spacer fabrics are produced and the pile thread forms the isolating and elastic intermediate element 48, are particularly suitable for producing such a formation.

Preferably the textile pressure sensor 46 is constructed such that the intermediate element 48 is directly knitted on to the first structure 30a which is conductive at least in regions by means of the thread 50. For this, the thread 50 is passed through the stitches of the structure 30a. Correspondingly, the second structure 30b which is conductive at least in regions is knitted onto the intermediate element 48 by means of the thread 42. In this manner, a three-dimensional textile pressure sensor 46 is produced which is formed completely from a coherent knitted fabric (or warp-knitted fabric). Alternatively, provision may be made for the first structure 30*a*, the second structure 30*b* and the intermediate element 48 to be formed as separate knitted fabrics which are stitched or glued to each other, instead of being formed as a coherent knitted fabric.

FIG. 4 shows a diagrammatic top view of a section of a structure 30*a* or 30*b* which is conductive at least in regions. FIG. 4 makes it clear how the conductive regions 34 are knitted on to the non-conductive region 32 by means of the thread 42. For this, the threads 42 are knitted with the thread 40 such that rows of stitches which are joined together are produced.

FIG. 5 shows an arrangement of two structures 30*a* and 30*b* which are formed to be conductive at least in regions for producing a textile pressure sensor 46. In FIG. 6, the conductive regions 32 of the structures 30*a* and 30*b* are arranged relative to each other such that their longitudinal axes L are arranged substantially at right-angles to one another. It goes without saying that a dielectric intermediate element 48 which is shown in FIG. 3 and cannot be recognised in FIG. 5 must be arranged between the structures 30*a* and 30*b* in order to produce the capacitive textile pressure sensor 46.

FIG. 5 makes it clear that, owing to the substantially right-angled arrangement of the web-like non-conductive regions 34 of the structures 30*a* and 30*b*, rectangular regions of overlap 52 arranged in a matrix result which in each case form a capacitor. In this manner, the number of capacitors formed may vary depending on the number of conductive regions 34.

FIG. 6 shows a further embodiment of the invention which is similar to the one according to FIG. 2. In this case, the conductive regions 34 are joined together via knitted-on non-conductive regions 32 to form the capacitor paths. The connectors 44 are likewise joined by knitting-on via non-conductive regions 32, so that a formation which as a whole is very stable is produced. In this case, it should however also be pointed out that the dimensions and dimensional relationships given in the drawings were selected thus merely for reasons of graphical illustration. Generally, of course, the connectors 44 are formed by very much narrower paths than the capacitor surfaces proper, which are formed by the conductive regions 34.

Overall, the present invention provides an advantageous pressure sensor which is designed to be flexible by means of a knitted fabric and can have many different uses. Furthermore, the pressure sensor according to the invention is particularly robust and comfortable, in particular when the pressure sensor is used in articles of clothing.

LIST OF REFERENCE NUMERALS 1 textile pressure sensor
3 first structure which is conductive in regions
5 second structure which is conductive in regions
7 dielectric intermediate element
9 conductive regions
11 points of overlap
13 compressive force
30, 30' structure which is conductive at least in regions
30*a* first structure which is conductive at least in regions
30*b* second structure which is conductive at least in regions
32 non-conductive region
34 conductive region
36 rows of stitches
38 rows of stitches
40 thread
42 thread
44 connectors
46 textile pressure sensor
48 intermediate element
50 thread
52 regions of overlap
C capacitor
L longitudinal direction

The invention claimed is:

1. A textile pressure sensor for the capacitive measuring of a pressure distribution of objects of any shape, in particular body parts, on a surface, comprising:
   the first structure including conductive regions which is conductive at least in regions, and
   the second structure including conductive regions which is conductive at least in regions,
   wherein the first and the second structure are separated from each other by a compressible dielectric intermediate element, and
   wherein the conductive regions of the first structure form capacitors with opposite conductive regions of the second structure, wherein the first and the second structure are designed as knitted fabrics and each includes a plurality of conductive regions which are joined together by knitted-on, non-conductive regions.

2. A textile pressure sensor according to claim 1, wherein the conductive regions of the knitted fabric comprise a plurality of adjacent rows of stitches of a conductive yarn or conductive filaments.

3. A textile pressure sensor according to claim 1, wherein the conductive paths of the first structure are arranged at an angle to conductive paths of the second structure, and the conductive paths form regions of overlap which are arranged in a matrix.

4. A textile pressure sensor according to claim 1, wherein the knitted fabric includes knitted-on connectors for joining the conductive regions to an electrical evaluation means.

5. A textile pressure sensor according to claim 1, wherein the dielectric intermediate element is designed as an elastically compressible knitted fabric.

6. A textile pressure sensor according to claim 1, wherein the dielectric intermediate element has integrated restoring elements in the region of the points of overlap.

7. A textile pressure sensor according to claim 6, wherein the integrated restoring elements are incorporated in the knitted fabric.

8. A textile pressure sensor according to claim 7, wherein the integrated restoring elements comprise a plurality of rows of stitches of a reversibly compressible knitted fabric and are arranged at least in the region of the points of overlap.

9. A textile pressure sensor according to claim 1, wherein the first and the second structure, and optionally also the dielectric intermediate element, consist of a single coherent knitted fabric optionally made of a plurality of different yarns.

10. A method for producing a textile pressure sensor for the capacitive measuring of a pressure distribution between an object and a surface, comprising:
    knitting together conductive regions for the formation of capacitor electrodes and/or connection tracks and isolating regions for the isolated joining of the capacitor electrodes.

11. A method according to claim 10, wherein the isolating regions are knitted on to the conductive regions.

12. A method according to claim 10, wherein further isolating regions for the formation of compressible capacitor dielectrics are knitted at least between opposite conductive regions which form capacitors.

13. A textile pressure sensor according to claim 2, wherein the conductive paths of the first structure are arranged at an angle to conductive paths of the second structure, and the conductive paths form regions of overlap which are arranged in a matrix.

14. A method according to claim 11, wherein further isolating regions for the formation of compressible capacitor dielectrics are knitted at least between opposite conductive regions which form capacitors.

* * * * *